United States Patent
Kleinberg

[11] Patent Number: 6,128,949
[45] Date of Patent: *Oct. 10, 2000

[54] PHASE CHANGE ANALYSIS IN LOGGING METHOD

[75] Inventor: Robert L. Kleinberg, Ridgefield, Conn.

[73] Assignee: Schlumberger Technology Corporation, Ridgefield, Conn.

[*] Notice: This patent issued on a continued prosecution application filed under 37 CFR 1.53(d), and is subject to the twenty year patent term provisions of 35 U.S.C. 154(a)(2).

[21] Appl. No.: 09/094,811

[22] Filed: Jun. 15, 1998

[51] Int. Cl.[7] .............................. E21B 47/10; G01R 3/00; G01V 1/40; G01N 7/00

[52] U.S. Cl. ................... 73/152.18; 73/19.03; 73/61.47; 73/61.79; 73/64.52; 73/590; 166/250.01; 166/309; 175/40; 175/50

[58] Field of Search ................................. 175/40, 48, 50; 73/152.16, 152.18, 152.23, 152.42, 152.55, 170.29, 19.05, 19.03, 61.46–61.49, 61.75, 61.79, 64.52, 597, 599, 590; 166/250.01, 252.4, 309

[56] References Cited

U.S. PATENT DOCUMENTS

| | | | |
|---|---|---|---|
| 2,380,082 | 7/1945 | Sloan | 73/152.18 |
| 4,092,858 | 6/1978 | Edgerton | 73/170.29 |
| 4,860,581 | 8/1989 | Zimmerman et al. | |
| 5,024,110 | 6/1991 | Doussiet et al. | |
| 5,329,811 | 7/1994 | Schultz et al. | |
| 5,473,939 | 12/1995 | Leder et al. | |
| 5,587,525 | 12/1996 | Shwe et al. | |
| 5,622,223 | 4/1997 | Vasquez . | |
| 5,635,631 | 6/1997 | Yesudas et al. | |
| 5,741,962 | 4/1998 | Birchak et al. | 73/152.16 |

OTHER PUBLICATIONS

John Michaels, Mike Moody, and Than Shwe, "Wireline Fluid Sampling", SPE 30610, 1995, pp. 871–878.
H. Ziegler and K. Rolf, "Quartz Sensor for Automatic Dew–Point Hygrometry", Sensors and Actuators, vol. 11, 1987, pp. 37–44.
Amyx, Bass, Whiting, "Petroleum Reservoir Engineering", McGraw–Hill, 1960, pp. 220–229.
A.W. Adamson, "Physical Chemistry of Surfaces", 3rd edition, Wiley, Chap. 8, 1976.
McGraw–Hill Encyclopedia of Science Technology Cavitation, pp. 317–320.
Abhijit Y. Dandekar and Erling H. Stenby, Measurement of Phase Behavior of Hydrocarbon Mixtures Using Fiber Optical Detection Techniques, SPE 38845, *1997 SPE Annual Technical Conference and Exhibition held in San Antonio, TX* (Oct. 5–8, 16997).

*Primary Examiner*—Hezron Williams
*Assistant Examiner*—J. David Wiggins
*Attorney, Agent, or Firm*—William B. Batzer; Mark Levy

[57] ABSTRACT

An improved method of fluid analysis in the borehole of a well. A fluid sampling tool is fitted with a pumpout module that can be used to draw fluids from the formation, circulate them through the instrument, and then expel this fluid to the borehole. It has been determined that certain measurements would be most valuable to implement down hole, such as the formation fluid bubble point and dew point. Accurate bubble point and dew point measurements are made by forming bubbles or a liquid drop in a measured sample, and detecting same.

15 Claims, 8 Drawing Sheets

PHASE CHANGE ANALYSIS IN LOGGING METHOD

FIELD OF THE INVENTION

The present invention relates to down hole fluid sampling tools and methods and, more particularly, to an improved fluid extraction tool and method for analyzing thermodynamic phases of complex fluids down hole.

BACKGROUND OF THE INVENTION

Schlumberger Technology Corporation, the assignee of the present invention, has pioneered the use of Modular Formation Dynamics Testers (MDTs) and other down hole tools. The Modular Formation Dynamics Tester is one of several very useful instruments for obtaining formation fluid samples. The MDT tool is suspended by a wire line and then lowered into the borehole of the well. The instrument is secured to the walls of the borehole and samples of the formation fluid are extracted. Such a tool is illustrated in U.S. Pat. No. 4,860,581, issued to Zimmerman et al on Aug. 29, 1989.

Fluid sampling tools comprise a pumpout module that can be used to draw fluids from the formation, circulate them through the instrument for analysis, and then expel these fluids to the borehole. The MDT can also retain samples of formation fluids in sampling bottles, which are then transported to the surface. The samples are transferred at the surface from the sampling bottles to transportation bottles. The formation fluid samples are then sent to pressure-volume-temperature laboratories (PVT labs) for analysis of their composition and their physical properties. Conventional PVT labs provide a broad range of measurements and services.

It is essential to know the bubble point of crude oil, because when the borehole pressure drops below the bubble point pressure during production, gas bubbles form in the porous rock reservoir. This dramatically decreases the oil phase relative permeability. Knowledge of the bubble point is also useful in determining the composition of the hydrocarbon mixture in the reservoir.

The best current practice of measuring bubble point is to bring a sample of fluid to the surface to be sent to a laboratory. There, the sample is placed in a cylinder, the volume of which is increased by a piston. Pressure is monitored by a gauge. The bubble point is normally considered to be the pressure at which a break (knee) appears in the pressure versus volume (P-V) curve.

However, this technique has several disadvantages. It is time consuming to bring a fluid sample to the surface, transfer it to the (possibly distant) laboratory, and await the result. Further limitations of this technique are: (1) only a few samples (typically six or fewer) can be transported to the surface on each tool run; (2) samples are altered by pressure and/or temperature changes when they are brought to the surface; (3) sample composition can change as a result of imperfect transfer from sampling bottle to transportation bottle, and to laboratory apparatus; (4) typically, a delay of several weeks occurs between the time of fluid sampling and the receipt of the laboratory report; (5) it is not known whether the sample and data are valid until long after the opportunity to take further samples passes; (6) high pressure, toxic, explosive samples must be transported, handled by wellsite and laboratory personnel, and disposed of, creating numerous potential health, safety and environmental problems.

The break in the aforementioned P-V curve is unreliable for determining the bubble point. A more reliable method is to observe bubble formation in the cylinder by use of a sight glass. In this manner, bubbles may be detected visually. They may also be measured by the transmission of near infrared light, since the bubble point is associated with attenuation of the light beam.

A number of down hole measurement techniques have been proposed for making a bubble point measurement within a down hole tool. These methods are described in U.S. Pat. Nos. 5,329,811; 5,473,939; 5,587,525; 5,622,223; and 5,635,631.

As described in the above-mentioned patents, fluid is isolated in the flow line, and then a pump (the same one used to extract fluid from the formation) is used to expand the volume. A pressure gauge is used to monitor the P-V curve.

Several problems exist with these prior art methods of determining bubble point. First, the measurement is very time consuming. At each stage of the expansion, it is necessary to allow bubbles to nucleate.

In U.S. Pat. No. 5,635,631, a gas is formed slowly, "relative to the amount of time taken to expand the sample." A full bubble point determination can require over an hour. Identifying a single pressure, following the maximum expansion, as the bubble point pressure, is clearly inaccurate, since it assumes that the compressibility of the hydrocarbon below the bubble point pressure is negligible. This assumption is erroneous, and can lead to substantial errors in bubble point pressure determination.

To detect phase changes of complex hydrocarbon mixtures, it is necessary to nucleate bubbles or drops of the new phase and to detect these bubbles. In standard laboratory apparatus, and in prior art down hole tools, the bubbles or drops are formed at arbitrary locations in the fluid volume, and then detected by pressure-volume measurements, or by detecting bubbles at another site (e.g., in the beam between a source and detector of light). Both of these methods are characterized by a delay between the arrival at the thermodynamic phase line and the initiation of phase change, and then a delay between the phase change and its detection. The methods and tools of this invention solve both problems.

In a related prior art publication [SPE 30610 (1995) Michaels (Western)] a technique is described in which the volume is increased as the pressure is monitored. Special significance is attached to the pressure at which the P-V curve departs from linearity. The authors cautiously declined to call this pressure the bubble point. This criterion may aid in collecting a sample for surface analysis, but it is not helpful in planning reservoir operations. This pressure may underestimate the bubble point, if the appearance of bubbles is delayed by retarded nucleation. Thus, maintaining the production pressure at this level during oil production may lead to formation of gas in the formation, and thus reduced productivity.

The present invention addresses a method of providing a down hole method of making rapid, accurate measurements of bubble point using a down hole tool, such as an MDT tool.

The dew point is the most important thermodynamic parameter associated with gas condensate reservoirs. Gas condensate reservoirs produce gas at high pressure. As the pressure drops, liquid is formed. When this happens in the pore space of the rock, the permeability to gas flow is greatly reduced, with accompanying loss of production. Therefore, it is important to maintain the pressure of gas condensate reservoirs above the dew point for as long as possible.

Sensors have been developed to measure the dew point of ordinary humid air. A cooled plate provides a definite location for the nucleation of liquid drops. The plate is part of a mass-sensitive sensor, such as an acoustic surface wave resonator, which detects the first presence of the liquid. H. Ziegler and K. Rolf, "Quartz Sensor for Automatic Dew-Point Hygrometry", Sensors and Actuators, Vol. 11, pp. 37–44 (1987).

Devices of this kind will often fail when used to measure the dew point of gas condensates under down hole conditions. This is so, because mixtures of hydrocarbons found in reservoirs can have unusual phase diagrams. As the pressure is reduced, the first condensation of liquid can occur at either the hottest or the coldest point accessible to the mixture. Amyx, Bass, Whiting, "Petroleum Reservoir Engineering", McGraw-Hill, 1960, pp. 220–229.

SUMMARY OF THE INVENTION

In accordance with the present invention, there is provided an improved method of fluid analysis in the borehole of a well. Fluid sampling tools as well as other down hole tools can be used to measure the bubble point and dew point of the extracted fluids. For example, an MDT tool comprises a pumpout module that can be used to draw fluids from the formation, circulate them through the instrument, and then expel this fluid to the borehole. It has been determined that bubble point and dew point measurements can be measured accurately with a down hole tool, such as an MDT.

To detect phase changes of complex hydrocarbon mixtures, it is necessary to nucleate bubbles or drops of the new phase and to detect these bubbles. In standard laboratory apparatus, and in prior art down hole tools, the bubbles or drops are formed at arbitrary locations in the fluid volume, and then detected by pressure-volume measurements, or by detecting bubbles at another site (e.g., in the beam between a source and detector of light). Both of these methods are characterized by a delay between the arrival at the thermodynamic phase line and the initiation of phase change, and then a delay between the phase change and its detection.

The solution proposed by this invention is to use an ultrasonic transducer in the fluid flowline to create bubbles by cavitation. Cavitation, however, is generally considered to be impossible when fluid pressure is high. Although several hundred psi is a rule of thumb for typical piezoelectric ultrasonic transducers, the pressure in the sampling tool flowline is as high as 20,000 psi. Therefore, it would appear that cavitation is not a viable method of creating bubbles down hole. However, for a fluid at the bubble point (i.e., the point at which bubbles are thermodynamically stable, but form slowly), modest localized pressure reductions, such as are found in acoustic waves, can lead to efficient evolution of bubbles.

The bubbles thus formed are detected at the site where they are produced by monitoring the ultrasonic properties of the liquid. This is conveniently done by monitoring the acoustic impedance of the ultrasonic transducers used to cavitate the fluid. At the first appearance of a bubble, even a transient bubble, the acoustic impedance mismatch between transducer and fluid is greatly altered. This in turn produces a change in the electrical impedance of the transducer.

Another method of nucleating bubbles at the bubble point is to provide predetermined locations in the fluid volume at which the temperature differs incrementally from that of the main body of liquid. For ordinary liquids, bubbles are preferentially formed where local hot spots occur in the liquid.

Crude oils differ from ordinary liquids in that they can have unusual phase diagrams. For some crudes, bubbles form preferentially at cold spots in the liquid volume. Thus, in order to be certain that the bubble point is accurately measured for all kinds of crude oils and crude oil mixtures, both a hot and a cold spot should be provided. A transducer placed in proximity to these hot and cold locations can sensitively detect the first appearance of bubbles.

No strong signature appears in the P-V characteristic at the dew point, because the first appearance of liquid does not substantially change the compressibility of the mixture. Therefore, it is necessary to sense the liquid phase directly. To do this, the first condensation must be on a moisture sensor.

Dew point sensors are normally integrated with coolers so that the first condensation occurs on the sensor. However, mixtures of hydrocarbons found in reservoirs can have unusual phase diagrams: condensation can occur at the hottest point accessible to the mixture. Amyx, Bass, Whiting, "Petroleum Reservoir Engineering", McGraw-Hill, 1960, pp. 220–229. Thus, moisture sensors must be mounted on both a heater and a cooler in order to ensure that the dew point will be measured accurately under all circumstances.

The method of the invention consists of the following steps:
 a) withdrawing a fluid sample from the formation fluid using a formation sampling tool, such as an MDT;
 b) closing valves in a flowline of the formation sampling tool in order to establish a well-defined sample volume;
 c) expanding this sample volume in step-by-step fashion (i.e., incrementally moving a piston of the pumpout module of the formation sampling tool);
 d) nucleating bubble formation or a drop of liquid at a predetermined site in the sampled volume;
 e) observing an onset of bubble formation or a drop of liquid at the predetermined site; and
 f) measuring pressure of fluid at the onset of bubble formation or a drop of liquid, which pressure measurement defines the bubble point or the dew point.

BRIEF DESCRIPTION OF THE DRAWINGS

A complete understanding of the present invention may be obtained by reference to the accompanying drawings, when considered in conjunction with the subsequent detailed description, in which.

DESCRIPTION OF THE PREFERRED EMBODIMENT

Generally speaking, the present invention features a method of determining the bubble point and dew point of formation fluids down hole. Extracting fluids from earth formations by means of sampling logging tools is widely known and practiced. "Schlumberger Wireline Formation Testing and Sampling" (1996). The best known commercial tools used for this purpose are the Schlumberger Modular Formation Dynamics Tester (MDT) and the Western-Atlas Reservoir Characterization Instrument (RCI).

Figure 1:
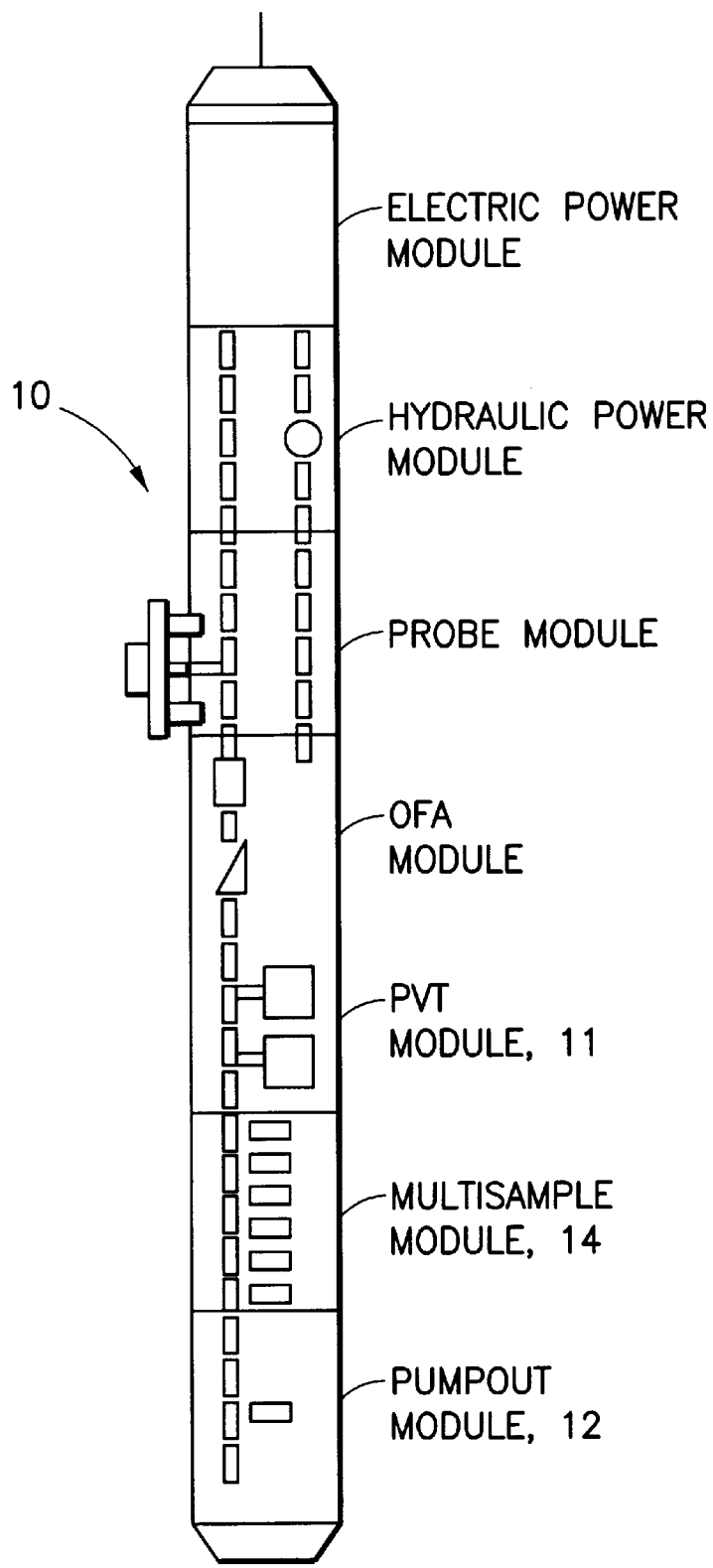
FIG. 1 illustrates a schematic view of a typical MDT tool that can be used for practicing the methods of the invention.

Now referring to FIG. 1, a typical MDT tool 10 having a PVT module 11 is shown.

For purposes of definition herein, tools that extract fluids from formations are generically called "sampling tools". Most commonly, sampling tools pump formation fluid for a substantial period of time in order to minimize contamination by mud filtrate. The MDT tool 10 has a pumpout module 12 for this purpose. During the pumping process, fluid properties are measured by various means, such as low-frequency electrical conductivity (MDT and RCI), dielectric constant (RCI) and/or optical properties (MDT). In the initial stage, this fluid is discarded by being pumped either into the borehole or back into the formation at a remote point. The fluid is redirected to one or more sample bottles in the sample module 14; subsequently, the fluid is transported in such bottles to the surface for extensive examination and testing, when contamination has been minimized. Alternatively, measurements of bubble point can be made inside the tool by the aforementioned patented methods.

There are two main problems with prior art, down hole bubble point and dew point measurements: the measurements are slow, and the measurements are inaccurate. The bubble point or dew point measurements are relatively time consuming. The bubble point measurement is impeded by bubbles that do not readily form at the thermodynamic bubble point of the liquid. Even when the gas phase is thermodynamically stable at a given temperature and pressure, a gas bubble may be unable to form because its surface free energy exceeds the free energy difference of the bulk phases. This phenomenon accounts for supercooling or superheating and is generally observed at first order phase transitions, described by classical nucleation theory. A. W. Adamson, "Physical Chemistry of Surfaces", 3rd edition, Wiley, chap. 8, 1976. In order to minimize the error associated with nucleation, bubble point measurements are made by changing the volume very slowly, typically over an hour.

Chemists have found that liquid-to-gas transitions can be observed more reproducibly when the liquid is stirred, but implementing that technique in the flowline of a down hole sampling tool would compromise reliability. Thus, the stirring procedure is not a preferred solution.

Figure 2:
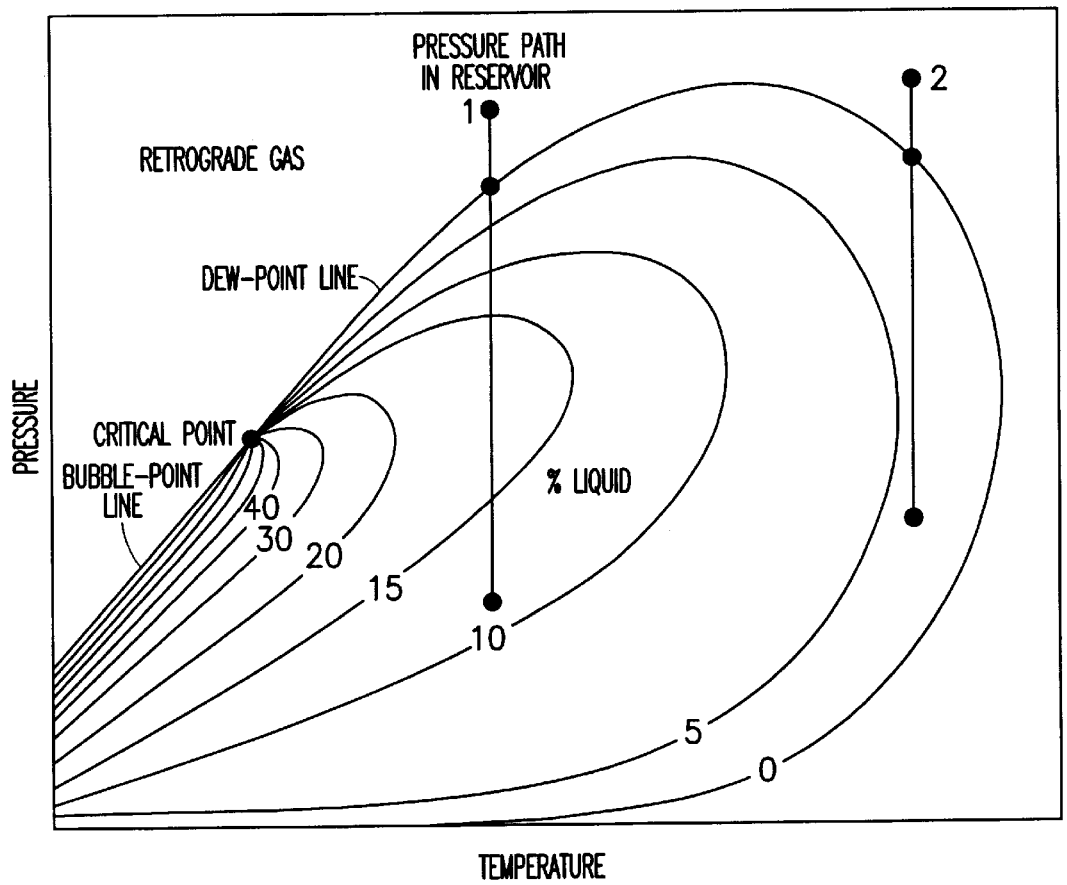
FIG. 2 depicts a graph of a phase diagram of a gas condensate reservoir.

Referring to FIG. 2, there is shown a typical phase diagram characterizing a gas condensate reservoir. The horizontal axis is temperature and the vertical axis is pressure. When a reservoir is first penetrated by a borehole, the reservoir is characterized by its original temperature and pressure. Two possible original states are shown, at Points 1 and 2. To bring the reservoir into production, the pressure is reduced at constant temperature. Thus, reservoir production is represented by movement down vertical lines in FIG. 2.

In order to maintain maximum permeability to hydrocarbon flow, it is essential that only one fluid phase exist in the formation. This means that the pressure must remain above the Dew Point Line shown in FIG. 2. Above this line, only gas exists; below the Dew Point Line, liquid condenses, forming a two-phase mixture in the rock pores of the earth formation. The presence of two phases decreases permeability to fluid flow, and therefore reduces production rate.

To detect the dew point pressure at down hole temperature using a fluid sampling tool, a sample of formation fluid is drawn into the tool at a pressure as close to formation pressure as possible. The sample in the tool is then isolated and the pressure reduced in a controlled manner, as described herein. When the dew point is reached, liquid condenses.

Ordinary dew point sensors used to measure atmospheric humidity are thermostated at a temperature slightly below the ambient temperature. The same technique is appropriate for reservoirs characterized by initial temperature and pressure conditions exemplified by Point 2 (FIG. 2). Condensation first appears at the cooled sensor, giving a reliable measurement of the dew point.

However, for gas condensate reservoirs characterized by initial conditions exemplified by Point 1 (FIG. 2), prior art sensors yield erroneous results. In that case, the cooled sensor is the last place in the volume on which liquid condenses. Therefore, it is necessary for the sensor to be placed at the warmest point in contact with the fluid to be tested. Liquid first condenses on the warm sensor, which therefore detects the first droplet of liquid resulting from the pressure reduction.

Figure 3:
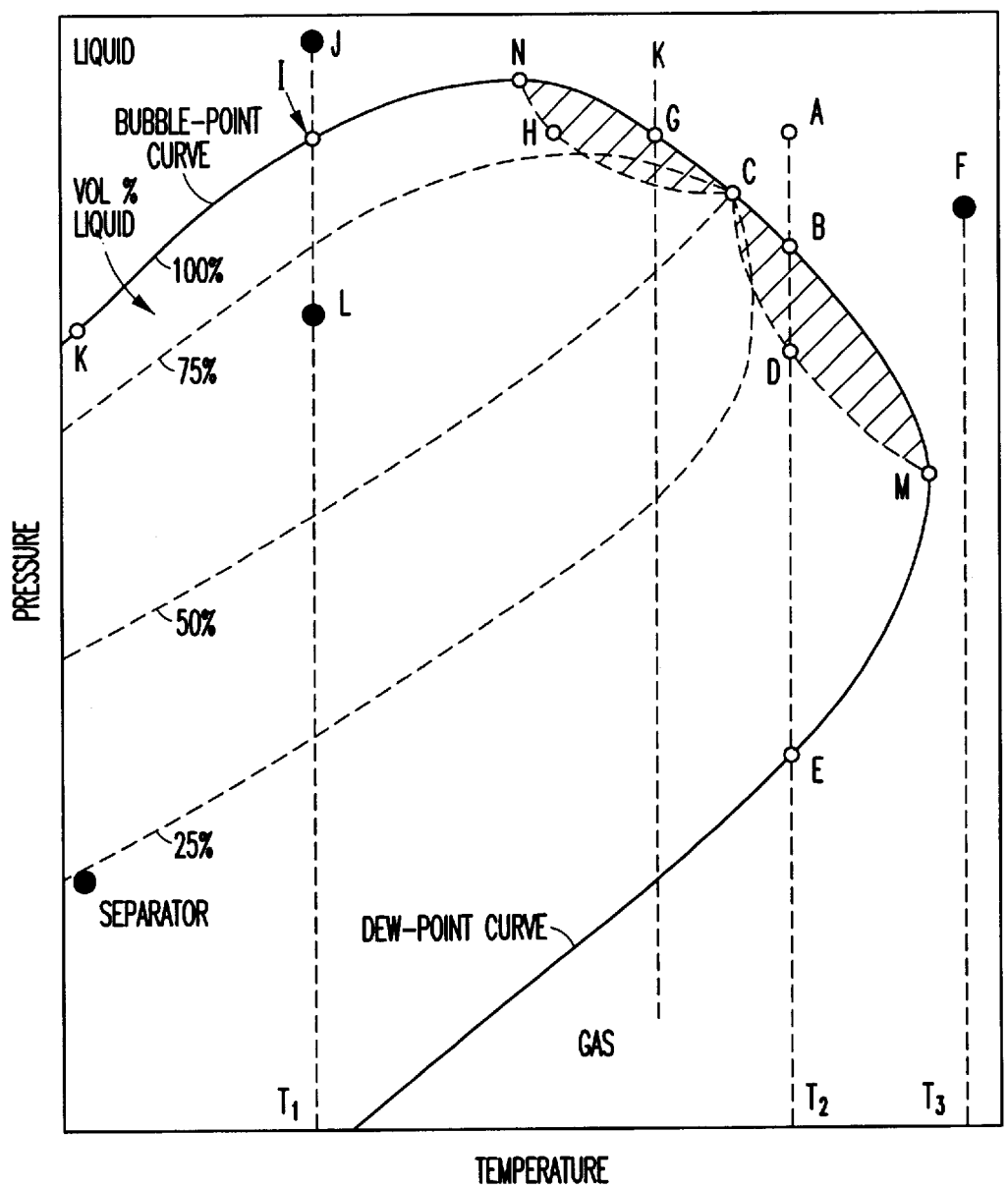
FIG. 3 shows a graph of a phase diagram of a crude oil with significant dissolved gas.

Referring now to FIG. 3, a typical phase diagram is illustrated of a crude oil reservoir with significant dissolved gas content. Once again, the horizontal axis is temperature and the vertical axis is pressure. When a reservoir is first penetrated by a borehole, the reservoir is characterized by its original temperature and pressure. Two possible original states are shown, at Points J and K. To bring the reservoir into production, the pressure is reduced at a constant temperature. Thus, reservoir production is represented by movement down vertical lines in FIG. 3.

As aforementioned, in order to maintain maximum permeability to hydrocarbon flow, it is essential that only one fluid phase exist in the formation. This means that the pressure must remain about the Bubble Point Curve shown in FIG. 3. Above this line, gas is completely dissolved in the oil; below the Bubble Point Curve, gas comes out of solution, forming a two-phase mixture in the rock pores of the earth formation. The presence of two phases decreases permeability to fluid flow, and therefore reduces production rate.

To detect the bubble point pressure at down hole temperature using a fluid sampling tool, a sample of formation fluid is drawn into the tool at a pressure as close to formation pressure as possible. The sample in the tool is then isolated and the pressure reduced in a controlled manner as described herein. When the bubble point is reached, free gas appears in the oil.

For many fluid mixtures, bubbles first appear in the fluid at the hottest point in the volume. In these fluids, a heater can be used to nucleate gas at a predetermined location. The same technique is appropriate for reservoirs characterized by initial temperature and pressure conditions exemplified by Point J (FIG. 3).

However, for those reservoirs characterized by initial conditions exemplified by Point K in FIG. 3, the warmest point is the last place in the volume at which bubbles form. Therefore, it is necessary for the bubble sensor to be placed at the coldest point in contact with the fluid to be tested.

Cavitation avoids the need to provide hot or cold points in bubble point cells. Bubbles first form at the location where sonic amplitude is greatest. Bubbles at the same place are readily detected by sonic means.

Figure 4:
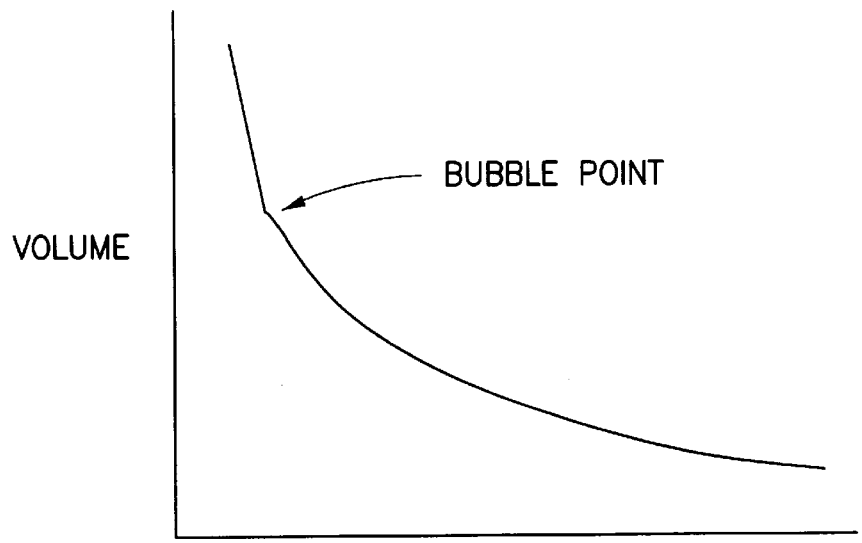
FIG. 4 illustrates a graph of a P-V curve for a complex hydrocarbon mixture at constant temperature, wherein no distinct slope change occurs at the bubble point.
Figure 5:
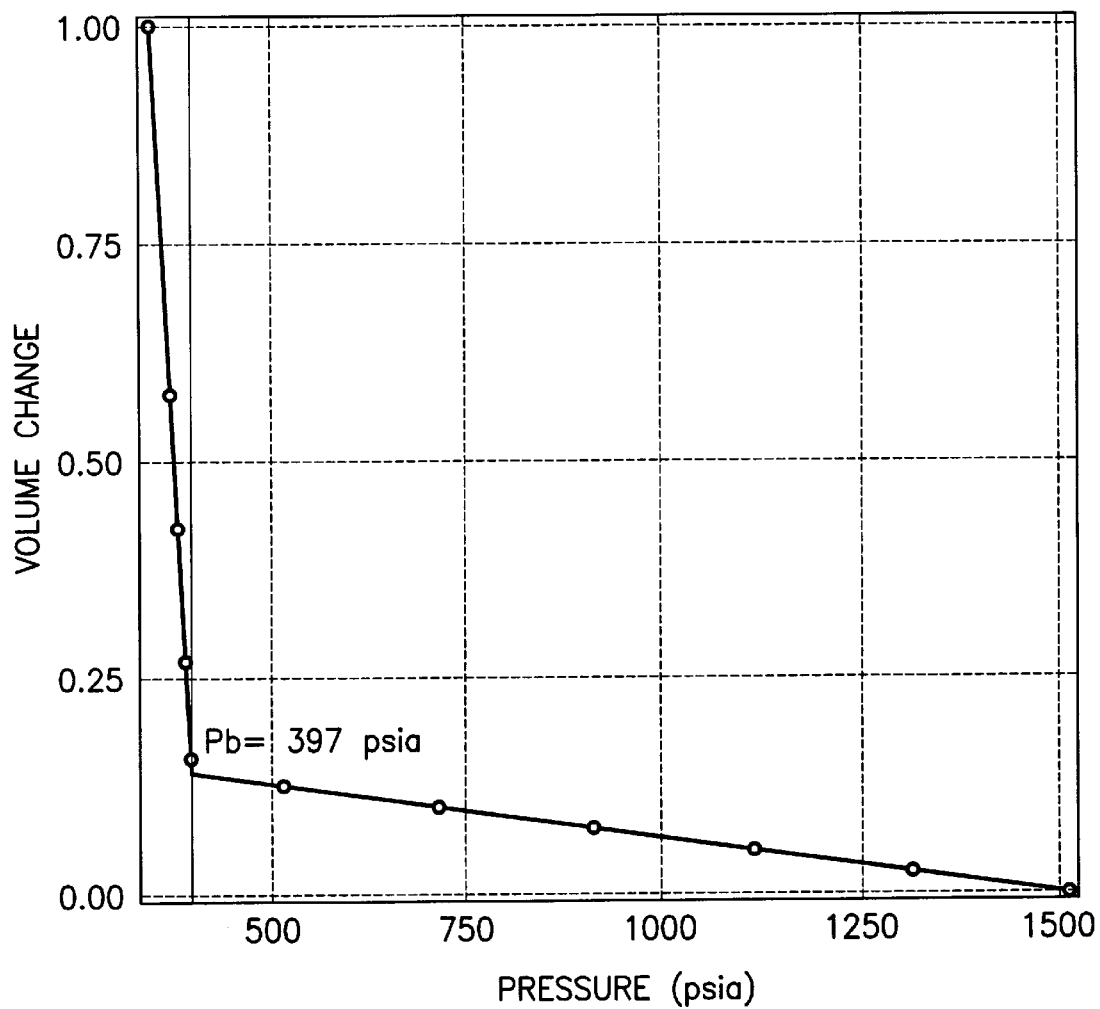
FIG. 5 depicts a graph of a P-V curve for a complex hydrocarbon mixture at constant temperature, wherein a distinct slope change occurs at the bubble point.

Referring to FIG. 5, it will be observed that for a complex hydrocarbon mixture at constant temperature, a distinct slope change may occur at the bubble point. However, this may not always be the case, as seen by the pressure-volume curve illustrated in FIG. 4.

The solution proposed by this invention is to use an ultrasonic transducer to create bubbles by cavitation. Cavitation, however, is generally considered to be impossible when fluid pressure is high. Although several hundred psi is a rule of thumb for typical piezoelectric ultrasonic transducers, the pressure in the sampling tool flowline is as high as 20,000 psi. Therefore, it would appear that cavitation is not a viable method of creating bubbles down hole. However, for a fluid at the bubble point (i.e., the point at which bubbles are thermodynamically stable, but form slowly), modest localized pressure reductions, such as are found in acoustic waves, can lead to efficient evolution of bubbles.

Various means may be used to induce cavitation, such as flow restrictions and propellers. The ultrasonic method is particularly suitable for sampling tools. The transducer may form part of the wall of the flowline. Deployed in such a manner, it does not interfere with other objectives of the sampling tool that rely on the unimpeded flow of fluid through the flowline. It is also relatively immune from erosion and has no moving parts, which are important considerations in down hole tools.

It is as important to sense the presence of bubbles as it is to generate them. Laboratory studies have shown that the pressure versus volume curve can be an unreliable bubble point indicator for many crude oils, as aforementioned. Thus, means (e.g., optical means) have been devised to sense the presence of bubbles directly. Such sensors can probe only a part (often only a small part) of the total volume of fluid, so these means depend on the bubbles being transported to the site of the sensor. This is one purpose of the stirring process often used in laboratories. A stirring mechanism can be a failure-prone component in a fluid sampling tool, and hence it is not included in the preferred mode of transporting samples to the site of a bubble sensor.

The solution proposed by this invention is to sense bubbles at the site at which they are produced. That is, bubbles are sensed at the location of the ultrasonic transducer used for cavitation. The acoustic impedance sensed by the ultrasonic transducer is extremely sensitive to the presence of bubbles, so bubbles can be produced and sensed at the same site, with very high reliability. The pressure of the fluid at which bubbles are first generated by the ultrasonic transducer is measured by a precision gauge, such as the Schlumberger CQG quartz pressure gauge.

The acoustic impedance of a material is defined as the product of its mass density and sound speed. In one implementation of the invention, the acoustic impedance of the transducer is approximately matched to the acoustic impedance of the fluid, in the absence of bubbles. At the first appearance of a bubble, both the density and the sound speed of the fluid decrease. The transducer and fluid are no longer impedance matched acoustically. Under this condition, the electrical impedance of the transducer increases.

Figure 6:
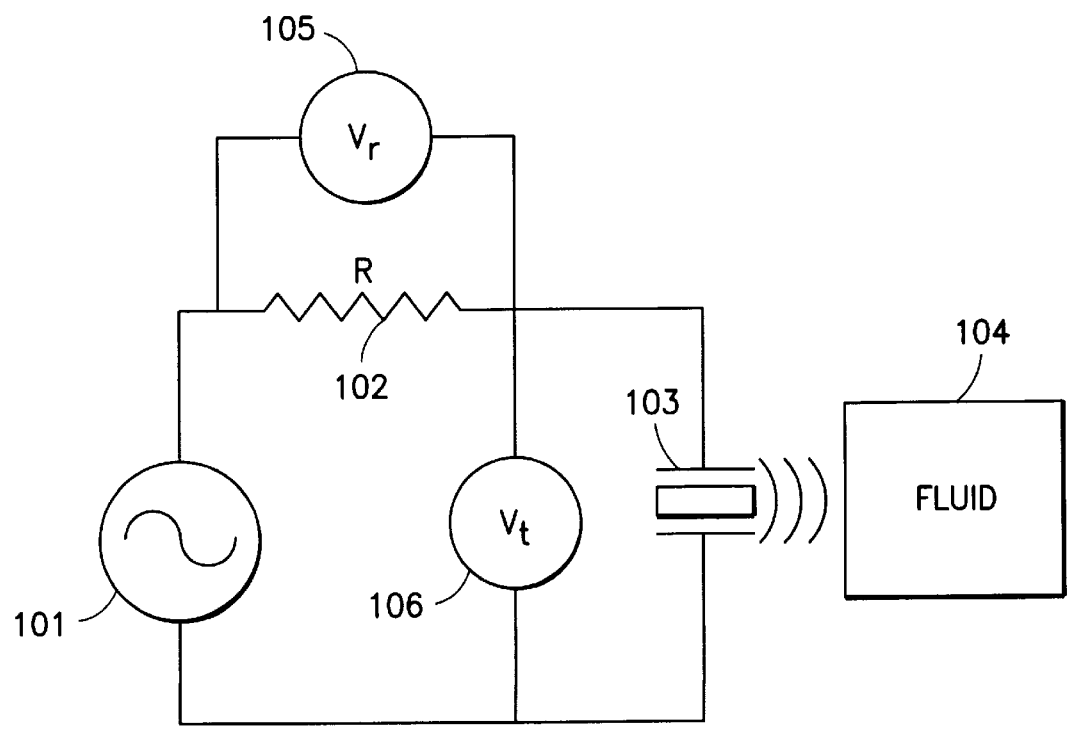
FIG. 6 is a schematic diagram of a simple electrical circuit for monitoring transducer impedance.

Referring to FIG. 6, there is shown a simple electrical circuit used to monitor the electrical impedance of the transducer. An electronic oscillator 101 drives alternating current through a resistor 102 (having fixed resistance, R) and an acoustic transducer 103. Transducer 103 radiates sound energy into fluid 104.

The current in the circuit, I, is monitored by using a high-impedance voltmeter 105 to measure the voltage, $V_r$, across resistor 102. Ohm's Law states that $I=V_r/R$.

The voltage across transducer 103, $V_t$, is monitored by a second voltmeter 106. The electrical impedance of the transducer 103 is $Z=V_t/I=(V_t/V_r)R$.

When the acoustic impedance of the transducer is matched to the acoustic impedance of the fluid, in the absence of bubbles, the voltage across the transducer is relatively low; the current is relatively high. Thus, the electrical impedance of the transducer is relatively low.

When the acoustic impedances of transducer and fluid are mismatched, however, in the presence of bubbles, the voltage across the transducer increases and the current decreases, increasing the electrical impedance.

Figure 7:
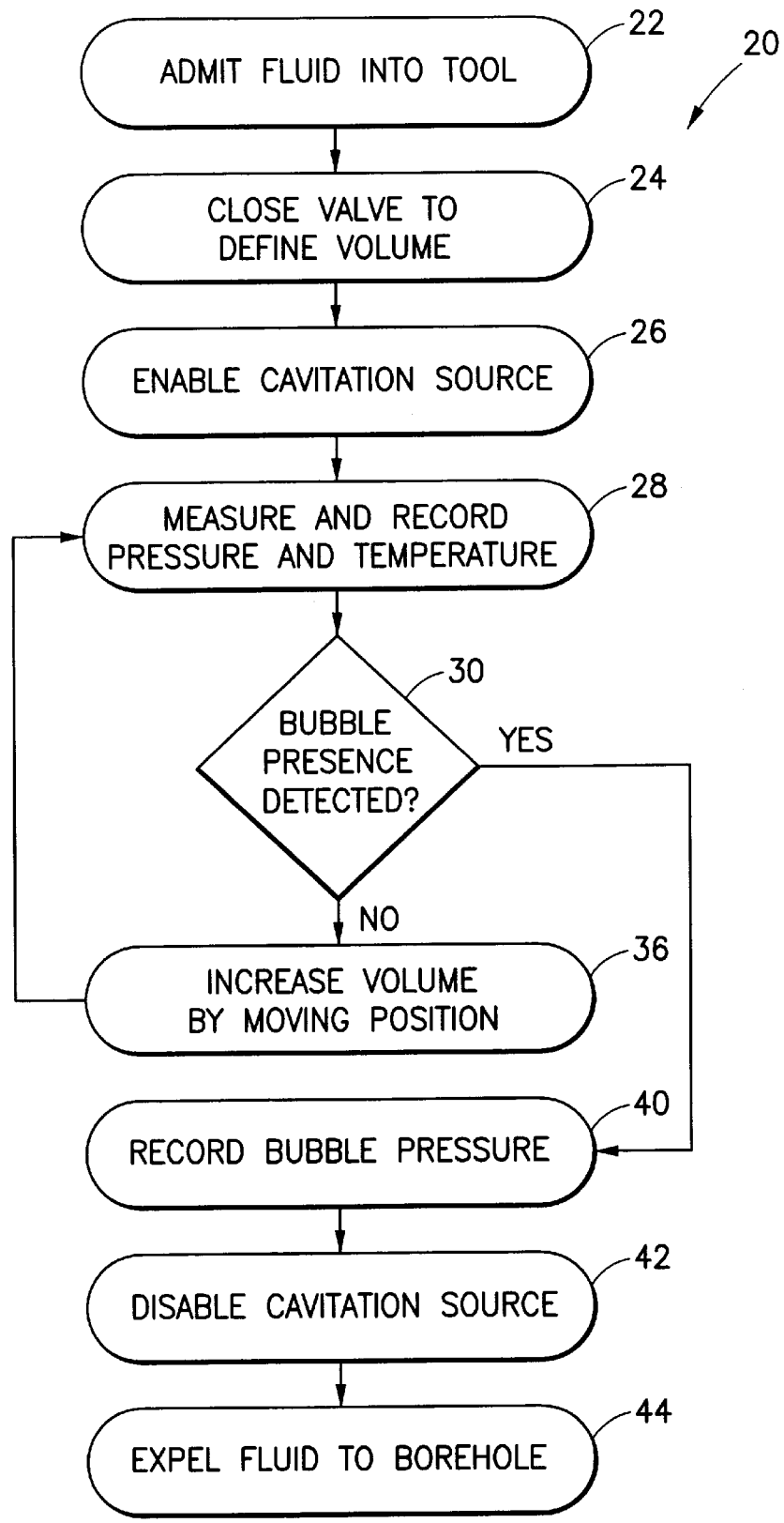
FIG. 7 illustrates a flow diagram for the method of bubble point measurement in accordance with the invention.

Referring to FIG. 7, a flow chart 20 is illustrated for the method of making a bubble point measurement, in accordance with the invention. The down hole fluid that is free of contamination is admitted into the tool, step 22. A valve in the tool is closed, step 24, in order to define a given volume. An ultrasonic transducer or other cavitation means is then enabled, step 26. The pressure and temperature of the sample fluid is measured, step 28. Then, the transducer is monitored to detect the presence of a bubble, step 30. If the bubble is detected, the bubble pressure is recorded, step 40. The cavitation source is then disabled, step 42, and the sampled fluid is expelled to the borehole, step 44. If a bubble is not detected for the given pressure and temperature, step 30, then the volume is increased by moving the piston of the sampling module, step 36. The sample is then remeasured for pressure and temperature, step 28. The detection process, defined by steps 30 through 44, is then repeated.

Figure 8:
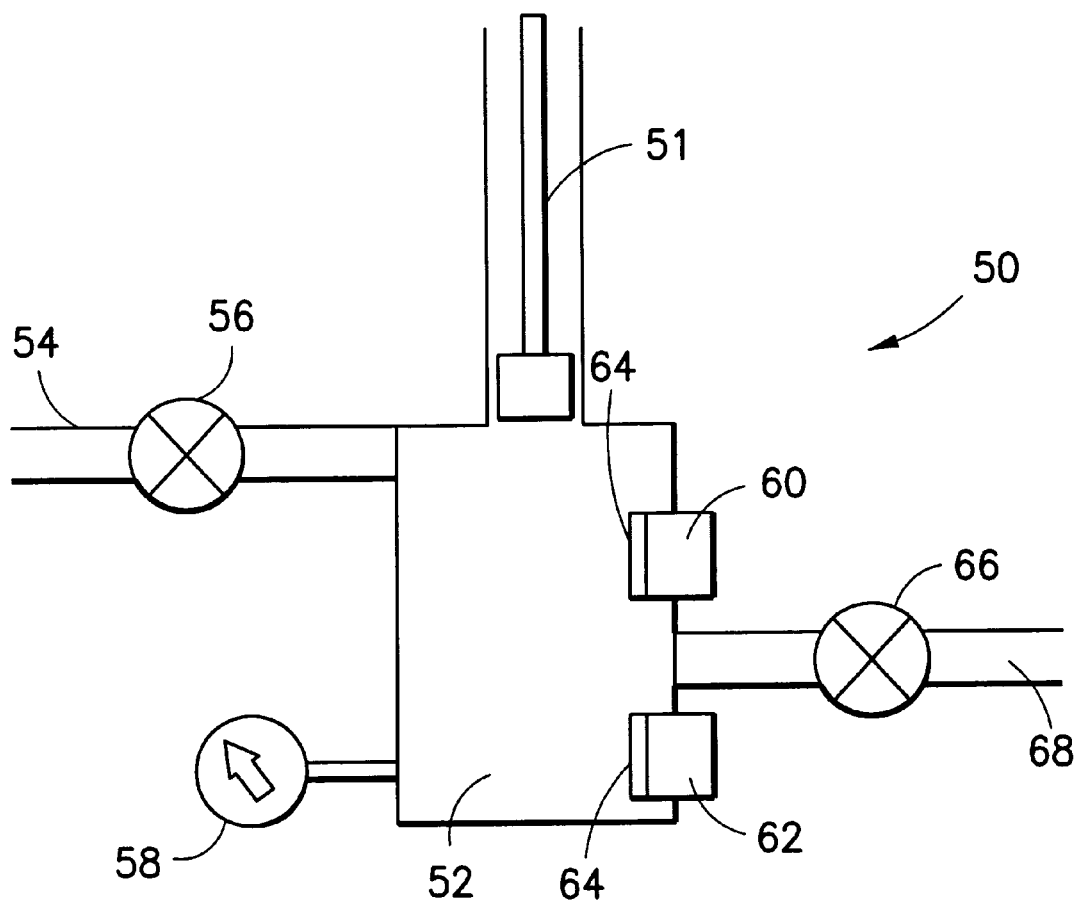
FIG. 8 depicts a schematic diagram of an apparatus for measuring the dew point in accordance with the method of the invention.

Referring to FIG. 8, an apparatus 50 for measuring the dew point down hole is illustrated. The fluid being sampled is drawn into a chamber 52 through a flow line 54 and inlet valve 56. The pressure gauge 58 measures the pressure in chamber 52. The pressure in the chamber 52 can be adjusted by piston 51. The temperature is also measured by suitable means (not shown). The Peltier cooler 60 reduces the temperature of the fluid at a selected site in chamber 52, while the heater 62 raises the temperature at another site. Liquid sensors 64 disposed at each site are used to detect the formation of a drop of liquid. After the measurements are taken, the sample is discharged to the borehole through the outlet valve 66 and flowline 68.

Figure 9:
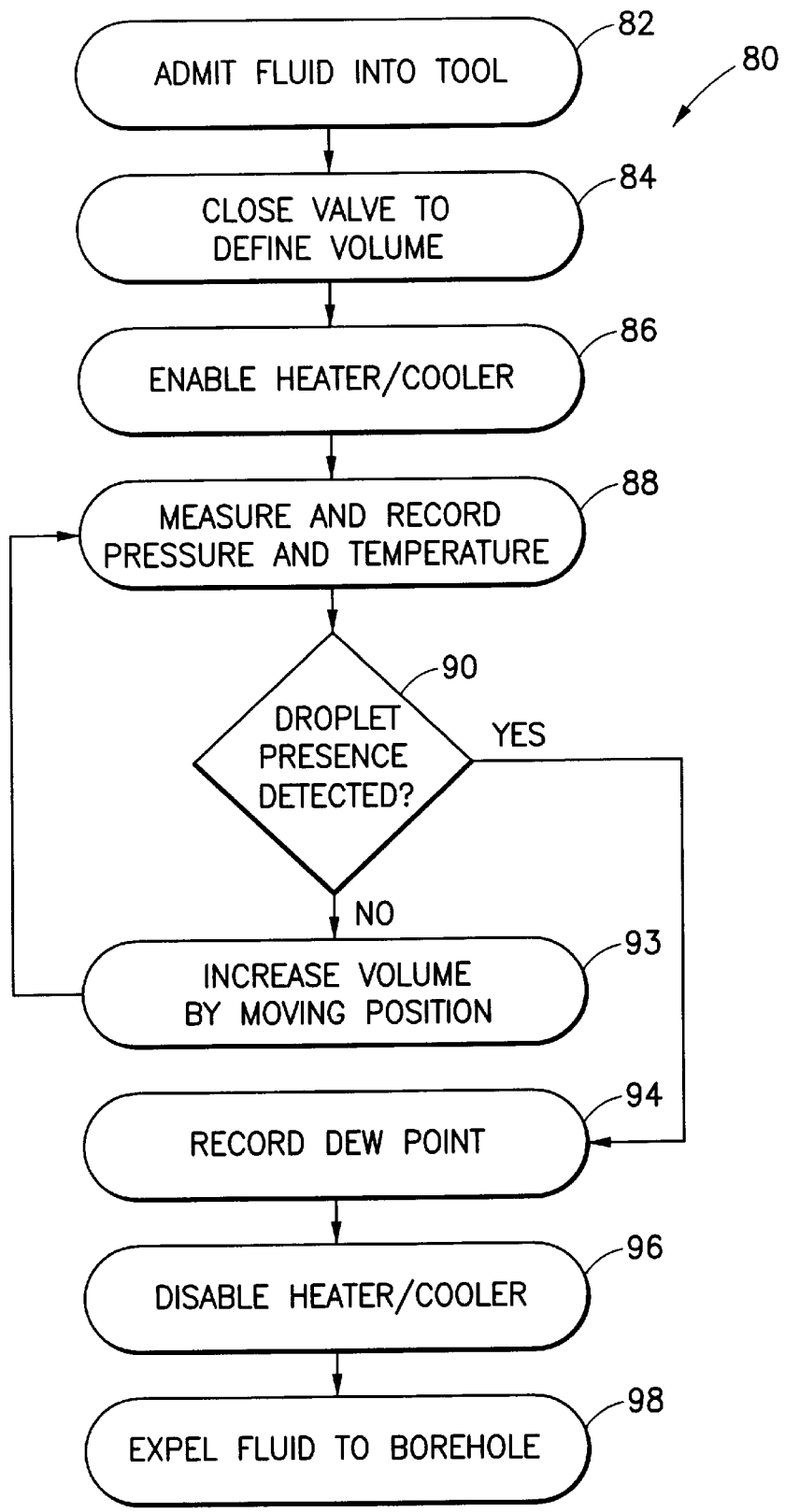
FIG. 9 shows a flow diagram for the method of dew point measurement in accordance with the invention.

Referring to FIG. 9, the method of measuring the dew point in accordance with the invention is illustrated by the flow chart 80. The fluid is admitted into the chamber 52, step 82. The valve 56 is closed to define the volume in chamber 52, step 84. The heater 62 and the cooler 60 are enabled, step 86. Pressure and temperature are measured, step 88. The sensors 64 monitor the presence of a liquid drop, step 90. If droplets are detected, then the dew point is recorded, step 94, the heater and cooler are disabled, step 96, and the fluid sample is expelled to the borehole, step 98. If no droplets are detected, step 90, then the volume of the fluid in chamber 52 is increased, step 93, and pressure and temperature are again measured, step 88. Then steps 90 through 98 are repeated.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. An in situ method of fluid analysis in the borehole of a well for determining phase characteristics of a formation fluid, comprising the steps of:
   a) withdrawing a fluid sample from said formation fluid using a formation sampling tool;
   b) establishing a well-defined sample volume;
   c) incrementally expanding the sample volume of step (b);
   d) nucleating bubble formation in said sample volume at fluid pressures greater than approximately 400 psi and approaching at least 20,000 psi by generating cavitation at a predetermined site;
   e) detecting an onset of bubble formation at said predetermined site; and
   f) measuring pressure of fluid at the onset of bubble formation in accordance with step (e), which pressure measurement defines a phase change of said formation fluid.

2. The method of fluid analysis of a formation fluid in accordance with claim 1, wherein said incrementally expanding the sample volume in accordance with step (c) further comprises the step of:
   g) incrementally moving a piston of a pumpout module of the formation sampling tool.

3. The method of fluid analysis of a formation fluid in accordance with claim 1, wherein said detection of detection step (e) is provided by an ultrasonic transducer.

4. An in situ method of fluid analysis in the borehole of a well for determining phase characteristics of a formation fluid, comprising the steps of:
   a) withdrawing a fluid sample from said formation fluid using a formation sampling tool;
   b) establishing a well-defined sample volume;
   c) incrementally expanding the sample volume of step (b);
   d) nucleating liquid drop formation in said sample volume at fluid pressures greater than approximately 400 psi and approaching at least 20,000 psi by generating cavitation at a predetermined site;
   e) detecting an onset of liquid drop formation thereby defining a dew point condition at said predetermined site; and
   f) measuring pressure of fluid at the onset of liquid drop formation in accordance with step (e), which pressure measurement defines a phase change.

5. The method of fluid analysis of a formation fluid in accordance with claim 4, wherein said incrementally expanding the sample volume in accordance with step (c) further comprises the step of:
   g) incrementally moving a piston of a pumpout module of the formation sampling tool.

6. An apparatus for determining a phase change in a fluid sample down hole of a borehole characterized by high temperature and high pressure conditions, comprising;
   flow sampling means for taking a fluid sample down hole;
   means associated with said sampling means for creating a phase change in said sample at fluid pressures greater than approximately 400 psi and approaching at least 20,000 psi at a given location; and
   detection means for detecting said phase change at at said given location.

7. The apparatus in accordance with claim 6, wherein said detecting means comprises an ultrasonic transducer.

8. The apparatus in accordance with claim 7, wherein said ultrasonic transducer comprises a piezoelectric ultrasonic transducer.

9. The apparatus in accordance with claim 6, wherein said means for creating a phase change comprises an ultrasonic transducer.

10. The apparatus in accordance with claim 9, wherein said ultrasonic transducer comprises a piezoelectric ultrasonic transducer.

11. An apparatus for determining a phase change in a fluid sample down hole of a borehole characterized by high temperature and high pressure conditions, comprising:
    sampling means for taking a fluid sample down hole;
    means associated with said sampling means for creating a phase change in said sample at fluid pressures greater than approximately 400 psi and approaching at least 20,000 psi by generating bubbles at a given bubble generating location in said apparatus; and detection means for detecting said phase change of said sample at said given bubble generating location.

12. The apparatus in accordance with claim 11, wherein said detecting means comprises an ultrasonic transducer.

13. The apparatus in accordance with claim 12, wherein said ultrasonic transducer comprises a piezoelectric ultrasonic transducer.

14. The apparatus in accordance with claim 11, wherein said means for creating a phase change comprises an ultrasonic transducer.

15. The apparatus in accordance with claim 14, wherein said ultrasonic transducer comprises a piezoelectric ultrasonic transducer.

* * * * *